(12) United States Patent
Kralovec et al.

(10) Patent No.: US 8,951,761 B2
(45) Date of Patent: Feb. 10, 2015

(54) IMMOBILIZED ENZYMES AND METHODS OF USING THEREOF

(75) Inventors: Jaroslav A. Kralovec, Halifax (CA); Weijie Wang, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 1688 days.

(21) Appl. No.: 11/918,150

(22) PCT Filed: Jun. 13, 2006

(86) PCT No.: PCT/IB2006/003999
§ 371 (c)(1),
(2), (4) Date: Dec. 18, 2007

(87) PCT Pub. No.: WO2007/102050
PCT Pub. Date: Sep. 13, 2007

(65) Prior Publication Data
US 2010/0041111 A9    Feb. 18, 2010

Related U.S. Application Data

(60) Provisional application No. 60/691,061, filed on Jun. 16, 2005.

(51) Int. Cl.
| | |
|---|---|
| *C12P 7/64* | (2006.01) |
| *C12N 9/20* | (2006.01) |
| *C12N 11/06* | (2006.01) |
| *C12N 11/08* | (2006.01) |

(52) U.S. Cl.
CPC ............... *C12P 7/6472* (2013.01); *C12N 9/20* (2013.01); *C12N 11/06* (2013.01); *C12N 11/08* (2013.01); *C12P 7/6436* (2013.01); *C12P 7/6454* (2013.01)
USPC ........................ 435/134; 435/174; 435/180

(58) Field of Classification Search
None
See application file for complete search history.

(56) References Cited

U.S. PATENT DOCUMENTS

| | | | | |
|---|---|---|---|---|
| 5,156,963 | A | 10/1992 | Eigtved | 435/135 |
| 5,569,594 | A | 10/1996 | Ikuta et al. | |
| 5,945,318 | A | 8/1999 | Breivik et al. | 435/134 |
| 6,518,049 | B1 | 2/2003 | Haraldsson et al. | 435/134 |
| 6,605,452 | B1 | 8/2003 | Basheer | 435/134 |
| 6,905,850 | B2 | 6/2005 | Irimescu et al. | 435/134 |
| 2004/0236128 | A1 | 11/2004 | Rubin | 554/174 |

FOREIGN PATENT DOCUMENTS

| | | |
|---|---|---|
| WO | WO 95/024459 | 9/1995 |
| WO | 9533047 A1 | 12/1995 |
| WO | WO 00/073254 | 12/2000 |
| WO | 01/62906 A2 | 8/2001 |
| WO | WO01/62906 | 8/2001 |
| WO | WO 2004/043894 | 5/2004 |

OTHER PUBLICATIONS

Supplemental European Search Report for European Patent Application No. 06847257 mailed Aug. 13, 2009.
Zuta et al., "Synthesis of acylglycerols for omega-3 fatty acids and conjugated linoleic acid isomers," *Biotech. Applied Biochem.* 43(1):25-32 (2006).
Ackman "Fish Oils," Bailey's Industrial Oil and Fat Products, Sixth Edition, John Wiley & Sons, pp. 279-317, 2005.
Balaji et al., "A facile and selective synthesis of β-keto esters via zeolite catalysed transesterification," *J Chem Soc Chem Commun* 1:707-708 (1996).
Berstein et al., "The protein data bank: A computer-based archival file for macromolecular structures," *J Mol Biol* 112(1):535-542 (1977).
Bikerstaft et al., "Immobilization of enzymes and cells. Some practical considerations," In Methods of Biotechnology. Immoblization of Enzymes and Cells, Bickerstaft Ed., Humana Press, Totowa, NJ, pp. 1-12, 1997.
Bimbo, "Technology of Production of Marine Oils" Marine Biogenic Lipids, Fats, and Oils, CRC Press, Inc. pp. 401-433, 1989.
Blossey et al., "Concerning the use of polymer based photosensitizers," *Tetrahedron Lett* 4:323-326 (1974).
Chavan et al., "Use of solid superacid (sulphated $SnO_2$) as efficient catalyst in facile transesterification of ketoesters," *Tetrahedron Lett* 37(2): 233-236 (1996).
El Hamby et al., "Preparation of non-polar lipids by high performance liquid chromatography on a cyanopropyl column," *J High Resol Chrom* 16:55-57 (1993).
Haken, "Studies in trans-esterification. Synthesis of n-alkyl methacrylates," *J Appl Chem* 13:168-171 (1963).
International Search Report, Written Opinion, and IPER for PCT/IB06/03999.
Komori et al., "Synthesis of polyoxyethylene derivatives of diesters of sucrose with long-chain fatty acids," *J Am Oil Chem Soc* 37:469-73 (1960).
Kosugi et al., "Synthesis of triacylglycerols from polyunsaturated fatty acid by immobilized lipase," *J Am Oil Chem Soc* 71(12):1397-1403 (1994).
Kralovec et al., "Production of ω-3 PUFA marine oil concentrates via enzymatic transesterification," 93rd AOCS meeting, Montreal, May 4-7, 2002.
Kris-Etherton et al., "AHA scientific statement: Fish consumption, fish oil, omega-3 fatty acids, and cardiovascular disease," *Circulation* 106:2747-2757 (2002).
Laszlo, "Catalysis of organic reactions by inorganic solids," *Pure Appl Chem* 62:2027-2030 (1990).
Marra, "The state of dietary supplements," *Nutr World* Nov. 32-40, 2002.
Mori et al., "Purified eicosapentaenoic and docosapentaenoic acids have different tial effects on serum lipids and lipoproteins, LDL particle size, glucose, and insulin in mildly hypelipidemic men," *Am J Clin Nutr*, 21:1085-1094 (2000).
NOAA Technical Memorandum, "Biomedical Test Materials Program: Production Methods and Safety Manual,", Jeanne D. Joseph, Oct. 1989.
O'Keefe and Harris, "Omega-3 fatty acids: Time for clinical implementation?" *Am J Cardiology*, 85:1239-1241 (2000).
Onuki et al., "In vivo effects of highly purified docosahezaenoic acid of rectal insulin absorption," *Int J Pharm* 198:147-156 (2000).
Otera, "Transesterification," *Che Review* 93: 1449-1470 (1993).

(Continued)

*Primary Examiner* — Kade Ariani
(74) *Attorney, Agent, or Firm* — Shannon McGarrah; Xi Chen (57) ABSTRACT

The disclosed matter relates to immobilized enzymes and methods of use thereof.

21 Claims, 2 Drawing Sheets

(56) References Cited

OTHER PUBLICATIONS

Ovide-Bordeaux and Grynberg, "Docosahexaenoic acid affects insulin-deficiency and inulin resistant-induced alterations in cardiac mitochondria," *Am J Physiol Regul Integr Comp Physiol*, 286:R519-27 (2003).

Posner et al., "Organic reactions at alumina surfaces. An extremely simple, convenient and selective method for acetylating primary alcohols in the presence of secondary alcohols," *Tetrahydron Lett* 22:5003-5006 (1981).

Seebach et al., "Titanate-mediated transesterifications with functionalized substrates," *Synthesis* 138-141 (1982).

Shimada et al., "Enzymatic purification of polyunsaturated fatty acids," *J Biosci Bioeng*, 91(6):529-538 (2001).

Taber et al., "Preparation of β-Keto esters by 4-DMAP-catalyzed ester exchange," *J Org Chem* 50:3618-3619 (1985).

Taft et al.,"The kinetics of the base-catalyzed methanolysis of Ortho, Meta and Para substituted *l*-menthyl benzoates," *J Am Chem Society* 72:4511-4519 (1950).

Trost, "The atom economy—a search for synthetic efficiency," *Science* 254:1471-1477 (1991).

Upperberg et al., "Crystallographic and molecular modeling studies of lipase B from *Candida antarctica* reveal a stereospecificity pocket for secondary alcohols," *Biochemistry* 34:6838 (1995).

Yazawa et al., "The reaction of carboxylic esters with boron tribromide a convenient method for the synthesis of amides and transesterificiation," *Tetrahydron Lett* 1823-1926 (1974).

Summons to Attend Oral Proceedings Pursuant to Rule 115(1) EPC for Application No. 06847257.0 dated Jun. 29, 2011.

Office Action for Application No. CL2020-2008 dated Dec. 19, 2011.

Response to Office Action for Application No. CL2020-2008 dated Apr. 9, 2012.

Decision to Refuse a European Patent Application No. EP06847257.0 dated Nov. 22, 2011.

Notice of Appeal for Application No. EP06847257.0 dated Jan. 27, 2012.

Grounds for Appeal for Application No. EP06847257.0 dated Apr. 2, 2012.

European Search Report for Application No. EP11189338.4 dated Mar. 7, 2012.

Extended European Search Report and Search Opinion for Application No. EP11189338.4 dated Mar. 13, 2012.

Office Action for U.S. Appl. No. 12/668,533 dated Mar. 14, 2012.

IMMOBILIZED ENZYMES AND METHODS OF USING THEREOF

CROSS REFERENCE TO RELATED APPLICATIONS

This application claims the benefit of priority to U.S. Provisional Patent Application 60/691,061, filed Jun. 16, 2005, which is incorporated by reference herein in its entirety.

FIELD

The disclosed matter relates to immobilized enzymes and methods of use thereof.

BACKGROUND

The beneficial effects of the long-chain polyunsaturated fatty acids (PUFA) that are characteristic of marine lipids, especially cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits and other biological effects. Among the most frequently mentioned benefits are those related to the prevention of and the treatment of inflammation, neurogenerative diseases, and cognitive development abnormalities. The public is becoming increasingly aware of the health benefits of fish oil and DHA and EPA concentrates, as it is evidenced from global sales of polyunsaturated fatty acids (PUFA). For instance, the sales of PUFA rose by 50% in 2002, and they were the only ones out of all categories of nutraceuticals that made a significant increase in sales.

Several methods of producing PUFA concentrates from marine oils are known, for example, selective lipase hydrolysis, PUFA complexation using urea (or more sophisticated molecular guest-host frameworks involving metric control), and a physical removal of unwanted components by fractionation. U.S. Publication No. 2004/0236128 describes the separation of EPA from DHA by precipitating EPA magnesium salt.

Fractionation involving molecular distillation is usually conducted on ethyl esters prepared from the starting triglycerides since they are more volatile than corresponding triglycerides. However, there is a controversy as to whether ethyl esters of PUFA are as bioavailable as their triglyceride counterparts. Therefore, there is a need to re-esterify the esters to the corresponding triglycerides.

The reaction describing the formation of triglycerides from the ethyl esters of fish oil is transesterification. Transesterification is a process where an ester is converted into another ester through interchange of the alkoxy moieties.

The reaction is an equilibrium process and the transformation occurs essentially by simply mixing the two components. However, it has been shown that the reaction is accelerated by Lewis acid catalysts (such as $BBr_3$, $AlCl_3$ etc., embedded in polystyrene-divinylbenzene), Bronsted acid catalysts such as HCl, $H_3PO_4$, $H_2SO_4$, p-TosOH, or basic catalysts such as metal alkoxides, metal hydroxides, and metal carbonates.

It has been apparent, however, that the transesterification reaction under these conditions does not meet in many cases the requirements of modern synthetic chemistry, i.e., highly efficient and regioselective reaction conditions. Thus efforts have continued to conduct transesterifications under milder conditions and to control randomization. Among the chemical catalysts developed, distanoxane was found to be effective for transesterification of various types of esters; however, this catalyst is difficult to prepare and is not commercially available, at least not in large quantities. The titanate-mediated transesterification method is extremely mild but fails to achieve certain kinds of transesterifications. Similarly, DMAP catalyzed reactions or reactions in the presence of tin-based superacids have different profiles of reaction selectivity. Successful attempts have also been made to perform transesterifications using zeolites, neutral chromatographic alumina, or kaolinites.

In spite of the advances in modern synthetic chemistry, the most popular industrial catalysts are strong bases. They are inexpensive, but because of their nature they generate a significant degree of side products, particularly at high temperatures necessary to achieve the desirable yields. In addition, they are not regioselective and lead to side reactions. Although they may be good choices for stable and structurally suitable chemical entities, they are not preferred for complex products such as, for example, fish oils. In the case of fish oils, enzymatically catalyzed transesterifications are a viable alternative, since they are regioselective and generate virtually no side products. However, their drawback is generally their cost.

Therefore, there is a need to transesterify complex esters such as, for example, polyunsaturated fatty acid esters to more useful esters. There is also a need for the efficient esterification of complex carboxylic acids such as fatty acids. The procedures should have a high efficiency with respect to transesterification and esterification and yet not produce undesirable side-products. The process should also be relatively inexpensive for commercial applications. Finally, the esters produced by the methods described herein should be ready to be incorporated into numerous food products without the requirement of removing additional impurities from the transesterification process. The immobilized enzymes and methods of use described herein satisfy these long-felt needs.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In a further aspect, the disclosed subject matter relates to immobilized enzymes and their methods of use.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitutes a part of this specification, illustrate several aspects described below.

DETAILED DESCRIPTION

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an unsaturated fatty acid" includes mixtures of two or more such unsaturated fatty acids, reference to "the matrix" includes mixtures of two or more such matrixes, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Reference will now be made in detail to specific aspects of the disclosed materials, compounds, compositions, articles, and methods, examples of which are illustrated in the accompanying Examples and Figures.

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components or residues A, B, and C are disclosed as well as a class of components or residues D, E, and F and an example of a combination compound A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Ocean Nutrition Canada, Ltd. (Dartmouth, Canada), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Immobilized Enzymes

Disclosed herein, in one aspect, are immobilized enzymes that comprise an esterification, transesterification, or interesterification/intraesterification enzyme immobilized in a food grade matrix. Each component of the disclosed immobilized enzymes is described below.

Enzymes

The enzymes useful herein are any naturally-occurring or synthetic enzymes that can be used to esterify a carboxylic acid or transesterify an ester. The term "esterify" is defined herein as the conversion of a carboxylic acid to the corresponding ester by reacting the carboxylic acid with an alcohol to produce the ester (e.g. $RCOOH+R^1OH \rightarrow RCOOR^1+H_2O$). The term "transesterify" is defined herein as the conversion of one ester to another by reacting the ester with an alcohol to produce a different ester (e.g., $RCOOR^1+R^2OH \rightarrow RCOOR^2+R^1OH$). The term "interesterify" is defined herein as the switching of ester moieties between two or more separate, independent esters. Interesterification between two esters is depicted in scheme 1A, where the $R^2$ and $R^4$ groups are switched in the starting materials (i.e., $R^1COOR^2$ and $R^3COOR^4$). Scheme 1B depicts the interesterification between a carboxylic acid ($R^1COOH$) and an ester ($R^3COOR^4$), which produces a new carboxylic acid and ester. The term "intraesterify" is defined herein as the switching of ester moieties within the same molecule. Intraesterification is depicted in scheme 1C, where the $R^2$ and $R^3$ groups are switched in the triester. Scheme 1D depicts the intraesterification between a carboxylic acid group and an ester within the same molecule, where hydrogen of the carboxylic acid switches with $R^3$ of the ester group.

Scheme 1

Suitable enzymes can be derived from a microorganism. Examples of microorganisms that can produce enzymes useful herein include, but are not limited to, *Burkholderia* sp., *Candida antarctica* B, *Candida rugosa*, *Candida cylindracea*, *Pseudomonas* sp., *Candida antarctica* A, *Porcine pancreas*, *Humicola* sp., *Humicola lanuginose*, *Mucor miehei*, *Rhizopus javan.*, *Pseudomonas fluor*, *Pseudomonas cepacia*, *Candida cylindrcae*, *Aspergillus niger*, *Rhizopus oryzae*, *Mucor jaanicus*, *Mucor javanicus*, *Rhizopus* sp., *Rhizopus japonicus*, *Rhizomucor miehi*, *Rhizopus niveus*, or *penicillium camembertii* (also *Rhizopus delemar*, *Pseudonomas*, *aeruginosa*).

In one example, the enzyme is produced from *Candida antarctica*. NOVOZYME™ CALB L is a lipase (lipase B) from *Candida antarctica* produced by submerged fermentation of a genetically modified *Aspergillus oryzae* microorganism. NOVOZYME™ CALB L is a highly versatile catalyst with activity towards a great variety of different substrates. The enzyme is used in particular as a powerful enantioselective catalyst in the synthesis of optically active alcohols, amines, and carboxylic acids. *Candida antarctica* lipase B is known to effectively convert ethyl esters or free fatty acids to triglycerides. This enzyme is a protein with 317 amino acid residues and molecular weight of 33,008 Daltons. The amino acids are assembled into 14α-helixes and 9β-sheets. The sequence and secondary structure of *Candida antarctica* lipase B are provided in SEQ ID NO:1.

It is also contemplated that derivatives of enzymes produced from microorganisms can be immobilized and used in the methods described herein. It is understood that the structure of many enzymes, as disclosed herein, are known and can be found, for example, at Genbank, and are herein incorporated by reference.

As all microbial lipases, CALB belongs to α/β hydrolases, the fold of which comprises of eight-stranded β-sheets sandwiched between two layers of amphiplilic α-helices. The mechanism of ester hydrolysis of these enzymes generally involves binding to the ester substrate, formation of the first tetrahedral intermediate by nucleophilic attack of the catalytic serine with the oxyanion stabilized by two or three H-bonds, the so-called oxyanion hole. The ester bond is cleaved and the acylated enzyme is hydrolyzed in the final step. The nucleophilic attack by the catalytic serine is mediated by the catalytic histidine and aspartic or glutamic acid residue. In certain examples, the longest fatty acid chain that completely binds inside the binding pocket of CALB is C13; thus, the scisille fatty acid binding site of this enzyme is relatively short (13.5 Å). The binding site of CALB is relatively short and has a small hydrophobic area located at the wall of the binding funnel. Structure of CALB has been published in the Protein Data Bank (The Protein Data Bank: a computer-based archival file for macromolecular structures. Bernstein et al., *J. Mol. Biol.* 112:525-542, 1977). It is also understood that the disclosed enzymes can be defined by their conserved catalytic cores which are understood in the art and are herein disclosed.

Sequence Similarities

It is understood that as discussed herein the use of the terms "homology" and "identity" mean the same thing as similarity. Thus, for example, if the use of the word homology is used between two non-natural sequences, it is understood that this is not necessarily indicating an evolutionary relationship between these two sequences but, rather, is looking at the similarity or relatedness between their sequences. Many of the methods for determining homology between two evolutionarily related molecules are routinely applied to any two or more nucleic acids or proteins for the purpose of measuring sequence similarity, regardless of whether they are evolutionarily related or not.

In general, it is understood that one way to define any known variants and derivatives or those that might arise of the disclosed genes and proteins herein, such as SEQ ID NO:1, is through defining the variants and derivatives in terms of homology to specific known sequences. This identity of particular sequences disclosed herein is also discussed elsewhere herein. In general, variants of genes and proteins herein disclosed typically have at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman, *Adv. Appl. Math.* 2:482, 1981, by the homology alignment algorithm of Needleman and Wunsch, *J. Mol. Biol.* 48:443, 1970, by the search for similarity method of Pearson and Lipman, *Proc. Natl. Acad. Sci. U.S.A.* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, *Science* 244:48-52, 1989, Jaeger et al., *Proc. Natl. Acad. Sci. U.S.A.* 86:7706-7710, 1989, Jaeger et al., *Methods Enzymol.* 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Hybridization/Selective Hybridization

It is also understood that the enzymes disclosed herein, such as SEQ ID NO:1, can be classified by the ability of the nucleic acids encoding them to hybridize with other nucleic acids. The term "hybridization" typically means a sequence driven interaction between at least two nucleic acid molecules, such as a primer or a probe and a gene. The phrase "sequence driven interaction" means an interaction that occurs between two nucleotides or nucleotide analogs or nucleotide derivatives in a nucleotide specific manner. For example, G interacting with C or A interacting with T are sequence driven interactions. Typically, sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some examples selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12 to about 25° C. below the $T_m$ (the melting temperature at which half of the molecules dissociate from their hybridization partners), followed by washing at a combination of temperature and salt concentration chosen so that the washing temperature is about 5° C. to about 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154:367, 1987, which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in, for example, 10, or 100, or 1000 fold excess. This type of assay can be performed at under conditions where both the limiting and non-limiting primer are, for example, 10 fold, or 100 fold, or 1000 fold below their $k_d$, or where only one of the nucleic acid molecules is 10 fold, or 100 fold, or 1000 fold, or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation; for example, if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example, if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Peptides

As discussed herein there are numerous variants and strain derivatives of the disclosed enzymes, such as SEQ ID NO:1 are known and herein contemplated. Enzymes can be made from proteins or peptides. Protein variants and derivatives are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues but can occur at a number of different locations at once; insertions usually will be on the order of from about 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables A and B and are referred to as conservative substitutions.

TABLE A

Amino Acid Abbreviations

| Amino Acid | Abbreviations |
|---|---|
| alanine | Ala (A) |
| alloisoleucine | AIle |
| arginine | Arg (R) |
| asparagine | Asn (N) |
| aspartic acid | Asp (D) |
| cysteine | Cys (C) |
| glutamic acid | Glu (E) |
| glutamine | Gln (Q) |
| glycine | Gly (G) |
| histidine | His (H) |
| isolelucine | Ile (I) |
| leucine | Leu (L) |
| lysine | Lys (K) |
| phenylalanine | Phe (F) |
| proline | Pro (P) |
| pyroglutamic acid | Glu |
| serine | Ser (S) |
| threonine | Thr (T) |
| tyrosine | Tyr(Y) |
| tryptophan | Trp (W) |
| valine | Val (V) |

TABLE B

Amino Acid Substitutions
Original Residue Exemplary Conservative Substitutions, others are known in the art.

Ala ↔ ser
Arg ↔ lys or gln
Asn ↔ gln or his
Asp ↔ glu
Cys ↔ ser
Gln ↔ asn or lys TABLE B-continued Amino Acid Substitutions
Original Residue Exemplary Conservative
Substitutions, others are known in the art.

Glu ↔ asp
Gly ↔ pro
His ↔ asn or gln
Ile ↔ leu or val
Leu ↔ ile or val
Lys ↔ arg or gln;
Met ↔ Leu or ile
Phemet ↔ leu or tyr
Ser ↔ thr
Thr ↔ ser
Trp ↔ tyr
Tyr ↔ trp or phe
Val ↔ ile or leu Substantial changes in function or immunological identity are made by selecting substitutions that are less conservative than those in Table B, i.e., selecting residues that differ more significantly in their effect on maintaining: (a) the structure of the polypeptide backbone in the area of the substitution, for example as a sheet or helical conformation; (b) the charge or hydrophobicity of the molecule at the target site; or (c) the bulk of the side chain. The substitutions that are generally expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the ω-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of a lipase. Specifically disclosed are variants of these and other proteins herein disclosed which have at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman, $Adv.$ $Appl.$ $Math.$ 2:482, 1981, by the homology alignment algorithm of Needleman and Wunsch, $J.$ $Mol.$ $Biol.$ 48:443, 1970, by the search for similarity method of Pearson and Lipman, $Proc.$ $Natl.$ $Acad.$ $Sci.$ $U.S.A.$ 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, $Science$ 244:48-52, 1989, Jaeger et al., $Proc.$ $Natl.$ $Acad.$ $Sci.$ $U.S.A.$ 86:7706-7710, 1989, Jaeger et al., $Methods$ $Enzymol.$ 183:281-306, 1989, which are herein incorporated by reference for at least for their material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular strain from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table A and Table B. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons to insert the analog amino acid into a peptide chain in a site specific way (Thorson et al, *Meth. Mol. Biol.* 77:43-73, 1991; Zoller, *Curr. Opinion Biotechnol.* 3:348-354, 1992; Ibba, *Biotechnol. Gen. Eng. Rev.* 13:197-216, 1995; Cahill et al., *TIBS* 14 (10):400-403, 1989; Benner, *TIB Tech* 12:158-163, 1994; Ibba and Hennecke, *Bio/technology* 12:678-682, 1994, all of which are herein incorporated by reference at least for their material related to amino acid analogs).

Molecules can be produced that resemble peptides, but which are not connected via a natural peptide linkage. For example, linkages for amino acids or amino acid analogs can include, but are not limited to, $CH_2NH$—, —$CH_2S$—, —$CH_2$—$CH_2$—, —$CH=CH$— (cis and trans), —$COCH_2$—, —$CH(OH)CH_2$—, and —$CHH_2SO$— (These and others can be found in Spatola, in Chemistry and Biochemistry of Amino Acids, Peptides, and Proteins, B. Weinstein, eds., Marcel Dekker, New York, p. 267, 1983; Spatola, Vega Data (March 1983), Vol. 1, Issue 3, Peptide Backbone Modifications (general review); Morley, *Trends Pharm. Sci.* 463-468, 1980; Hudson et al., *Int. J. Pept. Prot. Res.* 14:177-185, 1979 (—$CH_2NH$—, $CH_2CH_2$—); Spatola et al., *Life Sci.* 38:1243-1249, 1986 (—$CH_2$—S); Hann, *J. Chem. Soc Perkin Trans. I* 307-314, 1982 (—CH=CH—, cis and trans); Almquist et al., *J. Med. Chem.* 23:1392-1398, 1980 (—$COCH_2$—); Jennings-White et al., *Tetrahedron Lett.* 23:2533, 1982 (—$COCH_2$—); Szelke et al., European App. No. EP 45665 CA (1982): 97:39405 (1982) (—CH(OH) $CH_2$—); Holladay et al., *Tetrahedron. Lett.* 24:4401-4404, 1983 (—$C(OH)CH_2$—); and Hruby, *Life Sci.* 31:189-199, 1982 (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, *Ann. Rev. Biochem.* 61:387, 1992, which is incorporated herein by reference).

Food Grade Matrix

The term "food grade matrix" is any material that can form a matrix to immobilize an enzyme and that is cleared by the U.S. Food and Drug Administration as a Secondary Direct Food Additive under 21 C.F.R. §173. Sections 5-165 of 21 C.F.R. §173 provide representative examples of materials useful as the food grade matrix as well as permissible amounts of impurities to be considered a food grade matrix useful herein. For example, the material used to produce the food grade matrix comprises less than 10%, less than 8%, less than 6%, less than 4%, or less than 2% by weight non-polymerizable impurities.

In certain examples, the food grade matrix can comprise an acrylate-acrylamide resin (173.5), a polyacrylamide resin (173.10), an ion exchange resin (173.25), a perfluorinated ion exchange membrane (173.21), an ion exchange membrane (173.20), a molecular sieve resin (173.40), polymaleic acid or the sodium salt thereof (173.45), polyvinylpolypyrrolidone (173.50), polyvinylpyrrolidone (173.55), dimethylamine-epichlorohydrin copolymer (173.60), chloromethylated aminated styrene-divinylbenzene resin (173.70), sodium polyacrylate (173.73), or sorbitan monooleate (173.75), where the number in parenthesis is the federal registration section number that provides information with respect to the requirements of the material to be a secondary direct food additive.

In other examples, the food grade matrix can comprise a copolymer of divinylbenzene. For example, the food grade matrix can comprise a copolymer of (1) divinylbenzene and (2) acrylic acid, methacrylic acid, methyl acrylate, methyl methacrylate, ethyl vinyl benzene, or styrene. Title 21 C.F.R. §173.65 provides the requirements for the use of divinylbenzene copolymers as a secondary direct food additive. For example, the divinylbenzene copolymer must have at least 79 weight percent divinylbenzene and no more than 4 weight percent nonpolymerizable impurities. Examples of divinylbenzene copolymers useful herein as food grade matrices include, but are not limited to, AMBERLITE™ XAD16HP, AMBERLITE™ FPX600, AMBERLITE™ FPX66, and DUOLITE™ A7 all of which are manufactured by Rohm and Haas (Philadelphia, Pa.). AMBERLITE™ XAD16HP and FPX600 are crosslinked, macroporous polystyrene/divinylbenzene copolymers.

In one specific example, the enzyme is *Candida antarctica* lipase B and the food grade matrix is AMBERLITE™ XAD16HP.

Production of Immobilized Enzymes

The production of the immobilized enzyme generally involves admixing the enzyme with the material used to produce the food grade matrix in a solvent such as, for example, water. In one aspect, a surfactant is not used in the preparation of the immobilized enzyme. Immobilization parameters such as pH, temperature, duration of immobilization, etc. will vary depending upon the selection of the enzyme and food grade matrix material. After immobilization is complete, the solution is drained and the resultant enzyme-matrix can be washed with water or other suitable solvents. The selection of solvents for the preparation of the immobilized enzyme should be a material that is compatible with human consumption. Thus, water is a preferred solvent. After the enzyme has been immobilized, the enzyme-matrix can be dried under reduced pressure and/or at elevated temperature, or using other gas or liquid media ($N_2$, Ar, oil etc.).

The enzyme can be immobilized on the matrix via covalent or no-covalent (e.g., electrostatic, ionic, hydrogen bonding, adsorption, entrapment, encapsulation, etc.) attachments or bonds depending upon the selection of the enzyme and food grade matrix, as well as immobilization conditions. Not wishing to be bound by theory, it is believed that immobilization of the enzyme on the matrix renders the enzyme significantly more stable due to the fixation of the enzyme conformation. If possible, the enzyme should not leach from the matrix, which will increase the efficiency of the esterification, transesterification, or interesterification/intraesterification process as well as prolong the life of the immobilized enzyme for future use. It is also desirable that the enzymes attached to the surface of the matrix be such that the enzymes expose their catalytic center.

The amount of enzyme immobilized on the matrix can vary and will depend upon the enzyme and matrix selected and the end-use of the immobilized enzyme. In one aspect, the amount of enzyme immobilized in the matrix is from about 7.5 to about 35 KLU (kilo lipase units) per gram of matrix based on the difference in the enzyme concentration in the solution used to interact with the matrix, as measured at 280 nm. In other examples, the amount of enzyme immobilized on the matrix can be about 7.5, 8, 9, 10, 11, 12, 13, 14, 15, 16, 17, 18, 19, 20, 21, 22, 23, 24, 25, 26, 27, 28, 29, 30, 31, 32, 33, 34, or 35 KLU/g matrix, where any value can form an end-point of a range. In another example, the amount of enzyme immobilized in the matrix is from about 28 to about 32 KLU/g matrix.

Figure 1:
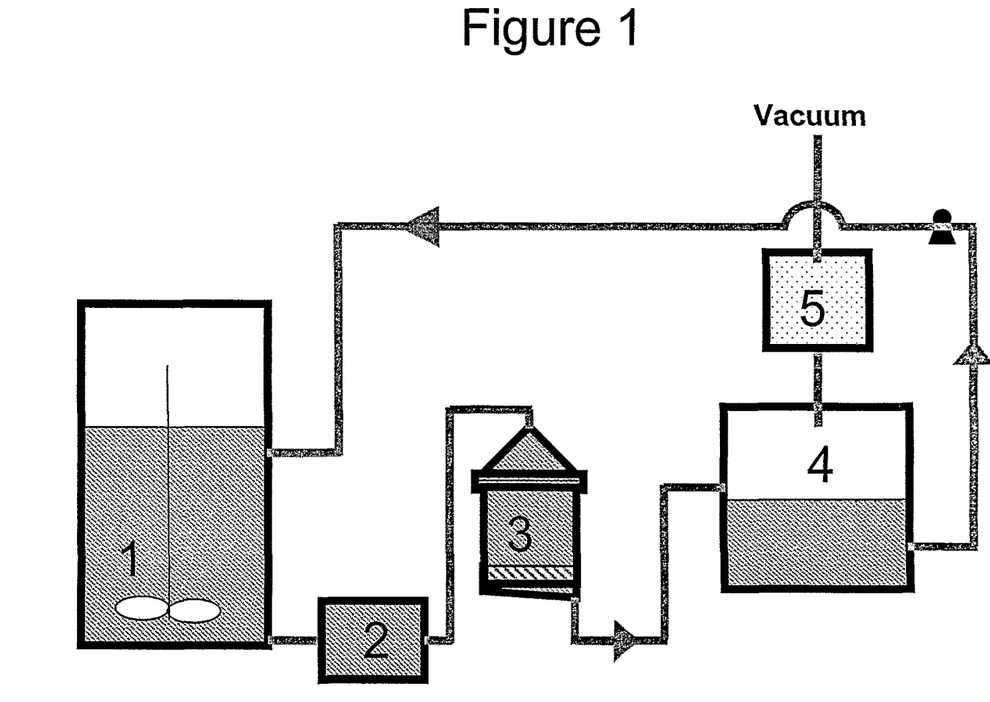
FIG. 1 is a schematic of a process for the enzymatic transformation of ethyl, esters (or free fatty acids) to triglycerides. In the figure, 1 represents a stirred heated holding vessel, 2 represents a shear pump, 3 represents a fixed-enzyme bed reactor (FEBR), 4 represents an evaporation tank, and 5 represents a condenser. The reactor 3 can be of varying geometry (e.g., length>height or length<height).
Figure 2:
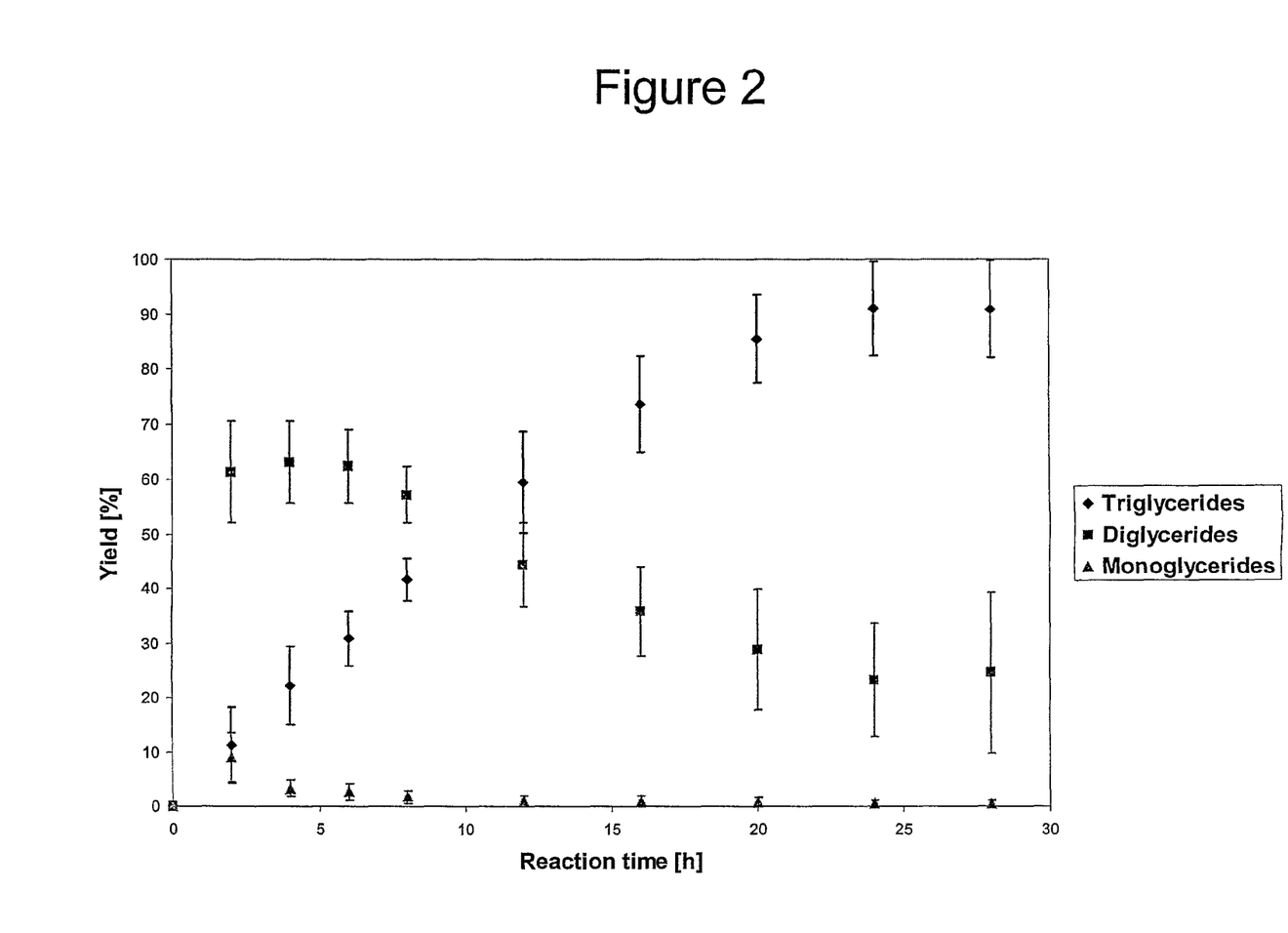
FIG. 2 is a graph of an enzymatic conversion of free fatty acids to triglyceride with a CALB enzyme immobilized on a food grade matrix (AMBERLITE™ XAD16HP). The same enzyme bed was used for 40 runs.

The immobilized matrix can be prepared by methods disclosed herein. In certain examples, the disclosed immobilized matrix can be prepared on a laboratory, pilot, or manufacturing scale. For example, the system shown in FIG. 1 can be used for the preparation of pilot and manufacturing scale immobilized enzymes. Further, more than one bed of enzyme can be used. That is, one can used processes where more than one fixed enzyme bed reactor containing the disclosed immobilized enzymes are connected in serial or parallel. The number of reactors will depend on the desired amounts of production and starting materials. Various geometries of enzyme reactors can also be used. Examples of suitable reactor geometries are shown in FIG. 1.

Use of Immobilized Enzymes

Described herein are methods for esterifying a carboxylic acid that comprise reacting the carboxylic acid with an alcohol in the presence of any of the immobilized enzymes described herein. In a further aspect, described herein are methods for transesterifying an ester that comprise reacting the ester with an alcohol in the presence of any of the immobilized enzymes described herein. In a still further aspect, described herein are methods for interesterifying two or more different carboxylic acids or esters thereof that comprise reacting the carboxylic acids or esters with each other in the presence of any of the immobilized enzymes described herein. In yet a still further aspect, described herein are methods for intraesterifying a compound comprising at least two ester groups or a compound comprising at least one carboxylic acid group and one ester group, that comprise contacting the compound with any of the immobilized enzymes described herein. A schematic of the transesterification of an ethyl ester (EE) to a triglyceride or an esterification of a free fatty acid (FFA) to a triglyceride is shown below.

Although the esterification of any carboxylic acid, the transesterification of any ester, the interesterification of two or more different carboxylic acids/esters, or the intraesterification of a compound is contemplated using the methods described herein, in many examples, a fatty acid or the ester there of can be used in any of the methods. In certain examples, the ester of the fatty acid is a $C_1$-$C_6$ branched or straight chain alkyl ester such as, for example, methyl, ethyl, propyl, butyl, pentyl, and the like.

In other specific examples, a fatty acid or the ester thereof can be used in the methods described herein. By "fatty acid" is meant a carboxylic acid with at least 10 carbon atoms. In one aspect, the fatty acid or the ester thereof can comprise at least 10, at least 12, at least 14, at least 16, at least 18, or at least 20 carbon atoms. In some specific examples, the fatty acid or the ester thereof can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In other examples, the fatty acid or the ester thereof can comprise a mixture of fatty acids or the esters thereof having a range of carbon atoms. For example, the fatty acid or the ester thereof can comprise from about 10 to about 40, from about 12 to about 38, from about 14 to about 36, from about 16 to about 34, from about 18 to about 32, or from about 20 to 30 carbon atoms.

The fatty acids or esters thereof can be saturated, unsaturated, or a mixture of saturated and unsaturated fatty acids. By "saturated" is meant that the molecule or residue contains no carbon-carbon double or triple bounds. By "unsaturated" is meant that the molecule or residue contains at least one carbon-carbon double or triple bond.

In one specific example, the fatty acids or the esters thereof can be derived from marine oils, such as fish oil, prior to esterification. Such oils typically contain mixtures of saturated and unsaturated fatty acids, but can be processed to result in a particular mixture of fatty acids (e.g., containing all saturated, all unsaturated, mixtures of both, or mixtures with fatty acids of a certain chain length or range of chain lengths). Any fish oil can be used in the disclosed compounds and methods. Examples of suitable fish oils include, but are not limited to, Atlantic fish oil, Pacific fish oil, Mediterranean fish oil, light pressed fish oil, alkaline treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, and shark oil, including mixtures and combinations thereof. Non-alkaline treated fish oil is also suitable. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed compositions and in the disclosed methods to prepare them. Further oils include, microbial oil, algal oil (e.g., oil from a dinoflagellate such as *Crypthecodinium cohnii*), fungal oil (e.g., oil from *Thraustochytrium, Schizochytrium*, or a mixture thereof), and/or plant oil, including mixtures and combinations thereof.

Examples of specific saturated fatty acids or esters thereof useful herein include, but are not limited to, capric acid (C10), lauric acid (C12), myristic acid (C14), palmitic acid (C16), margaric acid (C17), stearic acid (C18), arachidic acid (C20), behenic acid (C22), lignoceric acid (C24), cerotic acid (C26), montanic acid (C28), and melissic acid (C30), including branched and substituted derivatives thereof.

The unsaturated fatty acids or esters thereof suitable for the methods disclosed herein can comprise at least one unsaturated bond (i.e., a carbon-carbon double or triple bond). In one example, the unsaturated fatty acid or ester thereof can comprise at least 2, at least 3, at least 4, at least 5, at least 6, at least 7, at least 8, at least 9, or at least 10 carbon-carbon double bonds, triple bonds, or any combination thereof. In another example, the unsaturated fatty acid or ester thereof can comprise 1, 2, 3, 4, 5, 6, 7, 8, 9, or 10 unsaturated bonds, where any of the stated values can form an upper or lower endpoint when appropriate.

In one example, the unsaturated fatty acids or esters thereof can comprise one carbon-carbon double bond (i.e., a monoene acid or residue). Examples of unsaturated fatty acids or esters thereof that are suitable for the methods disclosed herein include, but are not limited to, those in the following Table 1.

TABLE 1

Examples of Monoene Acids

| Total number of carbon atoms in the fatty acid chain | Carbon number where double bond begins. ("c" denotes a cis double bond; "t" denotes a trans double bond) |
|---|---|
| 10 | 4c |
| 12 | 4c |
| 14 | 4c and 9c |
| 16 | 3t, 4c, 5t, 6c, 6t, 9c (palmitooleic), and 11c |
| 18 | 3t, 5c, 5t, 6c (petroselinic), 6t, 9c (oleic), 10c, 11c (cis-vaccenic), 11t (vaccenic), and 13c |
| 20 | 5c, 9c (gadolenic), 11c, 13c, and 15c |
| 22 | 5c, 11c (cetoleic), 13c (erucic), and 15c |
| 24 | 15c (selacholeic, nervonic) |
| 26 | 9c, and 17c (ximenic) |
| 28 | 9c, 19c (lumequic) |
| 30 | 21c |

In other examples, the unsaturated fatty acids or esters thereof can comprise at least two unsaturated bonds (e.g., polyene acids or residues). In some examples, the unsaturated fatty acids or esters thereof can comprise at least one pair of methylene interrupted unsaturated bonds. By "methylene interrupted unsaturated bond" is meant that one carbon-carbon double or triple bond is separated from another carbon-carbon double or triple bond by at least one methylene group (i.e., $CH_2$). Specific examples of unsaturated fatty acids or esters thereof that contain at least one pair of methylene interrupted unsaturated bonds include, but are not limited to, the n-1 family derived from 9, 12, 15-16:3; n-2 family derived from 9, 12, 15-17:3, 15:3, 17:3, 17:4, 20:4; n-3 family derived from 9, 12, 15-18:3, 15:2, 15:3, 15:4, 16:3, 16:4, 18:3 (α-linolenic), 18:4, 18:5, 20:2, 20:3, 20:4; 20:5 (EPA), 21:5, 22:3, 22:5 (DPA), 22:6 (DHA), 24:3, 24:4, 24:5, 24:6, 26:5, 26:6, 28:7, 30:5; n-4 family derived from 9, 12-16:2, 16:2, 16:3, 18:2, 18:3; n-5 family derived from 9, 12-17:2, 15:2, 17:2, 17:3, 19:2, 19:4, 20:3, 20:4 21:4, 21:5; n-6 family derived from 9, 12-18:2, 15:2, 16:2, 18:2 (linoleic acid), 18:3 (γ-linolenic acid); 20:2, 20:3, 20:4 (arachidonic acid), 22:2, 22:3, 22:4 (adrenic acid), 22:5, 24:2, 24:4, 25:2, 26:2, 30:4; n-7 family derived from 9-16:1, 15:2, 16:2, 17:2, 18:2, 19:2; n-8 family derived from 9-17:1, 15:2, 16:2, 17:2, 18:2, 19:2; n-9 family derived from 9-18:1, 17:2, 18:2, 20:2, 20:3, 22:3, 22:4; n-11 family 19:2, and the n-12 family 20:2.

In the above paragraph, the compounds are identified by referring first to the "n-x family," where x is the position in the fatty acid where the first double bond begins. The numbering scheme begins at the terminal end of the fatty acid where, for example, the terminal $CH_3$ group is designated position 1. In this sense, the n-3 family would be an omega-3 fatty acid, as described herein. The next number identifies the total number of carbon atoms in the fatty acid. The third number, which is after the colon, designates the total number of double bonds in the fatty acid. So, for example, in the n-1 family, 16:3, refers to a 16 carbon long fatty acid with 3 double bonds, each separated by a methylene, wherein the first double bond begins at position 1, i.e., the terminal end of the fatty acid. In another example, in the n-6 family, 18:3, refers to an 18 carbon long fatty acid with 3 methylene separated double bonds beginning at position 6, i.e., the sixth carbon from the terminal end of the fatty acid, and so forth.

Some other examples are fatty acids or esters thereof that contain at least one pair of unsaturated bonds interrupted by more than one methylene group. Suitable examples of these acids and esters include, but are not limited to, those in the following Table 2:

TABLE 2

Examples of Polyene Acids

| Total number of carbon atoms in the fatty acid chain | Carbon number where double bond begins. ("c" denotes a cis double bond; "t" denotes a trans double bond) |
|---|---|
| 18 | 5, 9 |
|  | 5, 11 |
|  | 2t, 9, 12 |
|  | 3t, 9, 12 |
|  | 5t, 9, 12 |
|  | 5, 9, 12 |
|  | 5, 11, 14 |
|  | 3t, 9, 12, 15 |
|  | 5, 9, 12, 15 |
| 20 | 5, 11 |
|  | 5, 13 |
|  | 7, 11 |
|  | 7, 13 |
|  | 5, 11, 14 |
|  | 7, 11, 14 |
|  | 5, 11, 14, 17 |
| 22 | 5, 11 |
|  | 5, 13 |
|  | 7, 13 |
|  | 7, 15 |
|  | 7, 17 |
|  | 9, 13 |
|  | 9, 15 |

Still other examples of unsaturated fatty acids or esters thereof that are suitable for use in the methods disclosed herein are those that contain at least one conjugated unsaturated bond. By "conjugated unsaturated bond" is meant that at least one pair of carbon-carbon double and/or triple bonds are bonded together, without a methylene ($CH_2$) group between them (e.g., —CH═CH—CH═CH—). Specific examples of unsaturated fatty acids or esters thereof that contain conjugated unsaturated bonds include, but are not limited to, those in the following Table 3.

TABLE 3

Examples of Conjugated Polyene Acids

| Total number of carbon atoms in the fatty acid chain. | Carbon number where double bond begins. ("c" denotes a cis double bond; "t" denotes a trans double bond) |
|---|---|
| 10 | 2t, 4t, 6c |
|  | 2c, 4t, 6t |
|  | 3t, 5t, 7c |
|  | 3c, 5t, 7t |
| 12 | 3, 5, 7, 9, 11 |
| 14 | 3, 5, 7, 9, 11 |
| 18 | 10t, 12t |
|  | 8c, 10t, 12c (jacaric) |
|  | 8t, 10t, 12c (calendic) |
|  | 8t, 10t, 12t |
|  | 9t, 11t, 13c (catalpic) |
|  | 9c, 11t, 13t (α-eleostearic) |
|  | 9c, 11t, 13c (punicic) |
|  | 9t, 11t, 13t (β-eleostearic) |
|  | 9c, 11t, 13t, 15c (α-parinaric) |
|  | 9t, 11t, 13t, 15t (β-parinaric) |

Omega-3 fatty acids and esters thereof are also useful in the methods described herein. Omega-3 fatty acids are unsaturated fatty acids that are particularly useful in the compounds and methods disclosed herein. Omega-3 fatty acids not only exhibit proven effects on lowering serum triglyceride levels, but they have strong connection to diabetes. For instance, docosahexaenoic acid (DHA) also has a strong insulin permeability enhancement effect, and it is viewed as a potential absorption enhancer for intestinal delivery of insulin (Onuki et al., *Int. J. Pharm.* 198:147-56, 2000). DHA intake prevents certain biochemical processes that originate from insulin deficiency (Ovide-Bordeaux and Grynberg, *Am. J. Physiol. Regul. Integr. Comp. Physiol.* 286:R519-27, 2003) and both DHA and EPA (eicosapentaenoic acid) significantly increase fasting insulin levels (Mori et al., *Am. J. Clin. Nutr.* 71:1085-94, 2000).

An omega-3 fatty acid is an unsaturated fatty acid that contains as its terminus $CH_3-CH_2-CH=CH-$. Specific examples of omega-3 fatty acids and esters thereof that are suitable for use herein include, but are not limited to, linolenic acid (18:3ω3), octadecatetraenoic acid (18:4ω3), eicosapentaenoic acid (20:5ω3) (EPA), docosahexaenoic acid (22:6ω3) (DHA), docosapentaenoic acid (22:6ω3) (DPA), derivatives thereof and mixtures thereof.

In still other examples, unsaturated fatty acids and esters thereof can be derived from a compound comprising the following formula:

wherein $R^1$ is a $C_3$-$C_{40}$ alkyl or alkenyl group comprising at least one double bond. The term "alkane" or "alkyl" as used herein is a saturated hydrocarbon group. The term "alkene" or "alkenyl" as used herein is a hydrocarbon group of at least 2 carbon atoms with a structural formula containing at least one carbon-carbon double bond. Asymmetric structures such as (AB)C=C(CD) are intended to include both the E and Z isomers (cis and trans). This may be presumed in structural formulae herein wherein an asymmetric alkene is present, or it may be explicitly indicated by the bond symbol C=C. In a further example, $R^1$ can be a $C_5$-$C_{38}$, $C_6$-$C_{36}$, $C_8$-$C_{34}$, $C_{10}$-$C_{32}$, $C_{12}$-$C_{30}$, $C_{14}$-$C_{28}$, $C_{16}$-$C_{26}$, or $C18$-$C_{24}$ alkenyl group. In yet another example, the alkenyl group of $R^1$ can have from 2 to 6, from 3 to 6, from 4 to 6, or from 5 to 6 double bonds. Still further, the alkenyl group of $R^1$ can have from 1, 2, 3, 4, 5, or 6 double bonds, where any of the stated values can form an upper or lower endpoint when appropriate.

Some specific examples of unsaturated fatty acids and esters thereof that can be used in the methods disclosed herein include, but are not limited to, linoleic acid, linolenic acid, γ-linolenic acid, arachidonic acid, mead acid, stearidonic acid, α-eleostearic acid, eleostearic acid, pinolenic acid, docosadienic acid, docosatetraenoic acid, docosapentaenoic acid, docosahexaenoic acid, octadecadienoic acid, octadecatrienoic acid, eicosatetraenoic acid, eicosapentaenoic, or any combination thereof. In one aspect, the unsaturated fatty acid ester can be derived from linolenic acid (18:3ω3), octadecatetraenoic acid (18:4ω3), eicosapentaenoic acid (20:5ω3) (EPA), eicosatetraenoic acid (20:40ω3), henicosapentaenoic acid (21:5ω3), docosahexaenoic acid (22:6ω3) (DHA), docosapentaenoic acid (22:5ω3) (DPA), including derivatives and mixtures thereof.

Additional examples of suitable unsaturated fatty acid and esters thereof that are suitable in the methods include, but are not limited to, allenic and acetylenic acids, such as C14: 2, 4, 5; C18: 5, 6 (laballenic); 5, 6, 16 (lamenallenic); C18: 6a (tarinic); 9a; 9a, 11t (ximenynic); 9a, 11a; 9a, 11a, 13c (bolekic); 9a, 11a, 13a, 15e, 8a, 10t (pyrulic) 9c, 12a (crepenynic); 9c, 12a, 14c (dehydrocrepenynic acid); 6a, 9c, 12c; 6a, 9c, 12c, 15c, 8a, 11c, 14c and corresponding Δ17e derivatives, 8-OH derivatives, and Δ17e, 8-OH derivatives.

Branched-chain acids and esters thereof, particularly iso-acids and anteiso acids, polymethyl branched acids, phytol based acids (e.g., phytanic, pristanic), furanoid acids are also suitable fatty acids, for use in the methods disclosed herein.

Still further, suitable fatty acids and esters thereof include, but are not limited to, cyclic acids, such as cyclopropane fatty acids, cyclopropene acids (e.g., lactobacillic), sterulic, malvalic, sterculynic, 2-hydroxysterculic, aleprolic, alepramic, aleprestic, aleprylic aleprestic, aleprylic alepric, hydnocarpic, chaulmoogric hormelic, manaoic, gorlic, oncobic, cyclopentenyl acids, and cyclohexylalkanoic acids.

Hydroxy acids and esters thereof, particularly butolic, ricinoleic, isoricinoleic, densipolic, lesquerolic, and auriolic are also suitable fatty acids that upon esterification can be used in the methods disclosed herein.

Epoxy acids and esters, particularly epoxidated C18:1 and C18:2, and furanoid acids and esters are further examples that can be used in the disclosed methods.

The alcohol used in any of the methods disclosed herein can be any alcohol. In one example, the alcohol is a polyol, which is defined as a compound having two or more hydroxyl groups. Examples of polyols useful herein include, but are not limited to, pentaerythritol, dipentaerythritol, tripentaerythritol, tetrapentaerythritol, tris(hydroxymethyl)ethane, or tris (hydroxymethyl)propane. In other examples, the alcohol is a sugar such as, for example, a glucosamine, a methyl glucoside, or other sugars such as, for example, sucrose. In another example, the polyol is glycerol.

The amount of carboxylic acid/ester and alcohol used will vary depending upon the acid, ester, and alcohol selected. In one example, a stoichiometric amount of carboxylic acid or ester relative to number of hydroxyl groups present on the alcohol can be used. For example, if the alcohol is a diol, then two molar equivalents of carboxylic acid or ester can be esterified or transesterified, respectively, with one molar equivalent of diol. An excess of alcohol can be used to achieve maximum esterification or transesterification as well as decrease the overall reaction time. In one aspect, when the alcohol is glycerol, the molar ratio of carboxylic acid or ester to alcohol is from 1:1 to 10:1, from 1:1 to 9:1, from 1:1 to 8:1, from 1:1 to 7:1, from 1:1 to 6:1, from 1:1 to 5:1, from 1:1 to 4:1, or from 1:1 to 3:1.

The amount of the immobilized enzyme (enzyme and matrix together) can also vary as well. In one example, the immobilized enzyme is from 0.1% to 20% by weight of total weight of carboxylic acid/ester and alcohol. In other examples, the enzyme is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20% by weight of the total reaction, where any value can form an endpoint of a range.

The carboxylic acid/ester, the alcohol, and the immobilized enzyme can be admixed with one another in any order. Depending upon the selection of the carboxylic acid/ester and the alcohol, it can be desirable to conduct the esterification or transesterification while the reaction mixture is stirred. For example, a solution of ester and alcohol can be added to one another under stirring followed by the addition of the immobilized enzyme. Also the reaction mixture could be forced to pass through the bed of immobilized enzyme and this could be executed either in continuous or batch (single or recycled) process.

In certain aspects, the esterification, transesterification, and interesterification/intraesterification reactions can take place at an elevated temperature. The precise elevated temperature can depend on the particular carboxylic acid or ester being used, the particular alcohol being used, the amount or concentration of the reagents, preference, and the like. Suitable temperatures at which the esterification and transesterification reactions can occur include, but are not limited to, from about 50° C. to about 100° C., from about 70° C. to about 90° C., from about 80° C. to about 90° C., or about 85° C. In another example, the esterification temperature can be from about 60° C. to about 70° C., or about 65° C. By varying the temperature it is possible to reduce reaction times depending upon the concentration of starting materials. Thus, reaction times can vary from 2 hours to 72 hours, 10 hours to 48, 10 hours to 36, 10 hours to 24 hours, 15 hours to 24 hours, 20 hours to 24 hours, or 22 hours.

In other examples, the method involves esterifying eicosapentaenoic acid 20:5ω3 (EPA), docosahexaenoic acid 22:6ω3 (DHA), docosapentaenoic acid 22:5ω3 (DPA), or any mixture thereof with glycerol, wherein the acid and the alcohol are present in a molar ratio of from about 2:1 to about 5:1, wherein the reaction is stirred in the presence of the immobilized enzyme at a temperature of from about 60° C. to about 90° C. for about 2 hours to about 24 hours, wherein the immobilized enzyme comprises an enzyme derived from *Candida antarctica* immobilized in a food grade matrix comprising a copolymer of divinylbenzene and styrene.

In another aspect, the method involves transesterifying an ethyl ester of eicosapentaenoic acid 20:5ω3 (EPA), docosahexaenoic acid 22:6ω3 (DHA), docosapentaenoic acid 22:5ω3 (DPA), or any mixture thereof with glycerol, wherein the ester and the alcohol are present in a molar ratio of from about 2:1 to about 5:1, wherein the reaction is stirred in the presence of the immobilized enzyme at a temperature of from about 70° C. to about 90° C. for about 20 hours to about 24 hours, wherein the immobilized enzyme comprises an enzyme derived from *Candida antarctica* immobilized in a food grade matrix comprising a copolymer of divinylbenzene and styrene.

As discussed above, esterification and transesterification enzymes can be expensive. Thus, ways to reuse the enzyme would be of commercial significance. The immobilized enzymes described herein can be reused several times. For example, after the esterification, transesterification, or interesterification reaction is complete, the solution can be filtered off and the immobilized enzyme can be and reused. The immobilized enzyme can be washed optionally with a suitable solvent and water, which can be desirable depending upon the selection of the ester and alcohol used. For example, if the acid/ester and/or alcohol clog the immobilized enzyme, then it would be desirable to wash off the ester or alcohol in order to increase the efficiency of the immobilized enzyme. In one example, water can be used to wash the immobilized enzyme. For the purpose of storage, the product could be stored in the presence of food preservatives, e.g., sodium benzoate, potassium sorbate, etc.

The methods described herein are efficient with respect to producing esters from carboxylic acids or other esters. For example, after the esterification, transesterification, or interesterification/intraesterification reaction is complete, the yield of ester relative to starting material is from about 70 to about 100%. In addition, because food grade matrices are used, the resultant transesters produced by the methods herein described do not require additional purification steps, do not produce unwanted side-products, and can be readily incorporated into food products, nutraceuticals, and pharmaceutical formulations, which are additional advantages of the disclosed methods and compositions. Still further, using the disclosed enzymatic methods to produce triglycerides of fatty acids, which are often more bioavailable than corresponding ethyl esters, can result in triglycerides that have better color and lower levels of trans-isomers, CDs, polymers, and side products. The disclosed methods can also result in esterified, transesterified, interesterified, and/or intraesterified products that have better sensory properties.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

X03020EE (30% EPA/20% DHA ethyl esters), XO0355EE (3% EPA/55% DHA ethyl esters), EE4020 (40% EPA/20% DHA ethyl esters), FFA4020 (40% EPA/20% DHA free fatty acids) were obtained from Ocean Nutrition Canada, Mulgrave Nova Scotia. The starting ethyl esters X03020EE and XO0355EE should be stored in airtight container with Teflon lining under nitrogen. Glycerol was at a purity of 99.5% purity. In Examples 2-5, NOVOZYME™ 435 manufactured by NOVOZYMES (Bagsvaerd, Denmark) was used. In the following examples, reactions with NOVAZYM™ 435 are considered comparative.

Example 1

Preparation of Immobilized Enzyme

The food grade matrix AMBERLITE™ XAD16HP (10 g, about 60% moisture) manufactured Rohm and Haas, was washed with water and suspended in 15 mL of solution containing 0.1% sorbic acid and 0.1% benzoic acid, pH 4.8 (prepared by mixing benzoic acid 1 g, sorbic acid 1 g, sodium hydroxide and distilled water (998 g)). A solution of *Candida antarctica* lipase B (30 mL at a 4.5:1 w/w ratio to matrix) was added and the mixture was gently stirred for 18 h at 20° C. The liquid was drained, the solid material washed with water, and finally dried at room temperature under vacuum at a pressure of less than 1 Torr for 16 hours.

Further immobilized enzymes were prepared as just described except that AMBERLITE™ FPX66 was used as the food grade matrix.

Example 2

Analysis of Esterification/Transesterification

These immobilized enzymes produced in Example 1 were tested to determine their ability to esterify fatty acids and to transesterify ethyl esters into triglycerides. The immobilized enzymes were loaded into a lab scale reaction vessel and the fatty acid or ethyl ester and alcohol were added to the immobilized enzyme. The amounts of triglyceride (TG) as well as di- and mono-glyceride (DG and MG, respectively) produced were analyzed. Lipid class was measured by normal phase high performance liquid chromatography (HPLC) coupled with evaporative light scattering detector (ELSD) using a YMC pack PVA-Sil column (150×4.6 mm, 5μ) or a Waters Spherisorb S3CN column (150×2 mm). The results are shown in Tables 4-7.

TABLE 4

FFA to TG conversion with enzyme immobilized on AMBERLITE ™ XAD16HP at 65-70° C. for 22 h.

| Trial | Components after reaction (%) | | | |
|---|---|---|---|---|
| | FFA | TG | DG | MG |
| 1 | 4.3 | 91.0 | 4.7 | 0.0 |
| 2 | 4.8 | 91.7 | 3.5 | 0.0 |
| 3 | 3.5 | 93.1 | 3.5 | 0.0 |
| 4 | 3.7 | 92.9 | 3.4 | 0.0 |

TABLE 5

EE to TG conversion with enzyme immobilized on AMBERLITE ™ XAD16HP for 24 hours

| Trial | Temp. | Components after reaction (%) | | | |
|---|---|---|---|---|---|
| | | EE | TG | DG | MG |
| 1 | 65-70° C. | 9.9 | 77.0 | 12.5 | 0.6 |
| 2 | 75-80° C. | 10.0 | 78.0 | 11.5 | 0.5 |
| 3 | 75-80° C. | 8.1 | 83.8 | 7.7 | 0.4 |
| 4 | 75-80° C. | 10.0 | 82.8 | 7.0 | 0.2 |

TABLE 6

FFA to TG conversion with enzyme immobilized on AMBERLITE ™ FPX66 at 65-70° C. for 22 hours

| Trial | Components after reaction (%) | | | |
|---|---|---|---|---|
| | FFA | TG | DG | MG |
| 1 | 11.9 | 78.6 | 9.6 | 0.0 |
| 2 | 9.0 | 86.7 | 4.3 | 0.0 |
| 3 | 8.5 | 87.0 | 4.6 | 0.0 |

TABLE 7

EE to TG conversion with enzyme immobilized on AMBERLITE ™ FPX66 at 75-80° C. for 23-24 hours

| Trial | Components after reaction (%) | | | |
|---|---|---|---|---|
| | EE | TG | DG | MG |
| 1 | 1.7 | 96.9 | 1.4 | 0.0 |
| 2 | 2.4 | 96.1 | 1.4 | 0.0 |
| 3 | 0.8 | 98.5 | 0.7 | 0.0 |
| 4 | 2.3 | 96.1 | 1.6 | 0.0 |

In further manufacturing scale example, the immobilized enzymes were loaded into fixed enzyme bed reactor and the fatty acid or ethyl ester and alcohol were pumped into the immobilized enzyme.

Example 3

Preparation of Large Scale Immobilized Enzyme

A large scale reactor system as shown in FIG. 1 was used. LIPOZYME™ CALB and distilled water were added to the holding vessel. AMBERLITE™ FPX66 food grade matrix was added to the fixed-bed enzyme reactor(s) (4000 kg and batch 8000 kg batches were run). The liquid enzyme mixture was recirculated through the matrix bed in the enzyme reactor for 24 hours or until protein samples leveled out and became consistent. The remaining enzyme solution was returned to the holding vessel. Filtered water was then pumped through the enzyme reactors to wash the immobilized enzymes. The remaining liquid enzyme was removed from the holding vessel.

Example 4

Large Scale Conversion of FFA to Triglycerides

FFA fish oil was added to the holding vessel of the system described in Example 3. The holding vessel was heated to 70° C.±5° C. While heating the vessel, agitation was started and glycerol was added. Once the addition of glycerol was complete, the contents of the holding vessel were agitated for 15 minutes. The enzyme reactor(s) containing the immobilized enzyme solution were prepared as in Example 3, and these can be re-used for several enzymatic conversions. The conversion cycle sequence began at this point for 24 hours. During this period, samples were taken and tested for % FFA every 3 hours. The conversion was complete when the % FFA was Max 15%. The oil was then pumped out and transferred to a feed tank where it awaited to undergo FFA stripping in an evaporation tank.

Example 5

Assays of Immobilized Enzyme Performance

Various other immobilized enzymes were prepared as described in Examples 1 and 3. These immobilized enzymes, as well as the immobilized enzyme produced in Examples 1 and 3, were tested to determine their ability to esterify fatty acids. The immobilized enzyme was loaded into a fixed enzyme bed reactor and the fatty acid and alcohol were pumped through the immobilized enzyme. The amounts of triglyceride (TG) as well as di- and mono-glyceride (DG and MG, respectively) produced were analyzed. The results are shown in Tables 8-10.

TABLE 8

(Comparative Example) Conversion of FFA 4020 to triglyceride (TG) with 2% immobilized NOVOZYME ™ CALB L on XAD-1180
Reaction conditions: ~3:1 FFA 4020 to glycerol at 65-70° C. for 21 hours

| No. of Trials | Immobilized Enzyme (enzyme:matrix) | Components after reaction % (average) | | | |
|---|---|---|---|---|---|
| | | FFA | TG | DG | MG |
| 2 | 3:1 lyophilized | 21.0 | 73.5 | 3.60 | 2.00 |
| 2 | 3:1 dried at 50° C. | 11.6 | 85.6 | 2.35 | 0.55 |
| 2 | 1.5:1 dried | 17.8 | 65.9 | 16.3 | 0.00 |
| 2 | 1:1 dried | 12.9 | 78.5 | 8.60 | 0.00 |
| 7 | 3:1 | 7.63 | 86.4 | 5.34 | 0.16 |
| 11 | 5:1 | 6.69 | 87.3 | 5.01 | 1.41 |

TABLE 9

(Comparative Example) Conversion of EE4020 to triglyceride (TG) with 2% immobilized NOVOZYME ™ CALB L on XAD-1180
Reaction conditions: ~3:1 EE4020 to glycerol at 80-85° C. for 22 hours

| No. of Trials | Immobilized Enzyme (enzyme:matrix) | Components after reaction % (average) | | | |
|---|---|---|---|---|---|
| | | FFA | TG | DG | MG |
| 1 | 5:1 | 11.7 | 62.4 | 25.4 | 0.5 |
| 4 | 1.5:1 | 39.3 | 6.03 | 43.8 | 10.7 |

TABLE 10

Conversion of FFA 4020 to triglyceride (TG) with 2% immobilized NOVOZYME ™ CALB L on various matrixes
Reaction conditions: ~3:1 FFA4020 to glycerol at 65-70° C. for 22 hours

| Matrix | Enzyme/ water (W/W) | Enzyme/ wet beads (W/W) | No. of Trials | Components after reaction % (average) | | | |
|---|---|---|---|---|---|---|---|
| | | | | FFA | TG | DG | MG |
| XAD16HP | 1.5:1 | 3:1 | 4 | 6.9 | 87.88 | 4.78 | 0.00 |
| XAD761 | 2:1 | 3:1 | 2 | 18.2 | 59.8 | 22.1 | 0.05 |
| XAD4 | 2.25:1 | 3:1 | 1 | 76.0 | 0.9 | 10.4 | 10.5 |
| Comparative Examples | | | | | | | |
| XAD16 | 2:1 | 3.5:1 | 1 | 4.3 | 94.5 | 1.2 | 0 |
| XAD16 | 2.25:1 | 3:1 | 4 | 19.7 | 63.6 | 16.0 | 0.56 |
| XAD16 | 2:1 | 2.67:1 | 2 | 23.7 | 49.9 | 24.7 | 0.95 |
| XAD16 | 2.5:1 | 3.33:1 | 2 | 27.3 | 41.1 | 28.9 | 2.30 |
| XAD16 | 3:1 | 3.33:1 | 1 | 18.8 | 71.8 | 9.40 | 0.00 |
| XAD16 (5% KCl washed) | 2.3:1 | 3:1 | 2 | 91.0 | 0.15 | 6.55 | 2.60 |
| XAD16 (1% KCl washed) | 23:1 | 3:1 | 2 | 73.0 | 0.50 | 19.2 | 7.40 |
| XAD1180 | 2.25:1 | 3:1 | 2 | 7.7 | 92.4 | 1.65 | 0.2 |
| KO₂CCH₃ | | 20% | 1 | 51.3 | 0.5 | 38.0 | 10.1 |
| NOVOZYME ™ 435 | | | 1 | 8.00 | 90.7 | 1.20 | 0.00 |

Example 6

(Comparative Example) Transesterification Using NOVOZYM™ 435

The oil XO0355 EE (55 g), together with glycerol (5 g), was placed in a reaction vessel and NOVOZYME™435 (1.2 g) was added. A vacuum (<1 mbar) was applied and the temperature was raised to 85° C. The reaction mixture was stirred at this temperature and pressure for 22 hours, then the product was separated from the immobilized enzyme and the residual immobilized enzyme was ready to be used in the next batch.

Example 7

Effect of Varying Reaction Conditions

Reactivity of ethyl ester fish oil was investigated under varying reaction conditions (Table 11). The higher ratios of ethyl ester to glycerol (e.g., 4.5-1) were tested to confirm previous findings. The reaction was repeated with EE/glycerol ratios of 3.5:1 but only at temperatures around 60° C. with 61% yield of TGs and 25% EEs remaining in average. A molar ratio: 2.8:1 after 22 hours at 70° C. led to the final mixture consisting of EE 6.3%, TG 78.6%, DG 12.2%, MG 2.8%, at 60-65° C. However, the yields were considerably lower in two other separate experiments, when the temperature was lower.

TABLE 11

(Comparative) Transesterification of ethyl ester concentrates to the corresponding triglycerides with 2% NOVOZYME ™ 435.

| EE/ Glycerol molar ratio | Incubation temperature | Time (total) | Components after reaction % (average) | | | | |
|---|---|---|---|---|---|---|---|
| | | | TG | DG | MG | EE | % TG* |
| R1-3.5:1** | 56-60° C. (mostly 56°) | 22 h | 59.1 | 12.6 | 1.5 | 26.8 | 80.7 |
| R2-3.5:1 | 65° C. | 22 h | 67.1 | 4.9 | 0.6 | 27.4 | 92.4 |
| R4-3.5:1 | 58-60° C. (mostly 58°) | 22 h | 44.1 | 19.4 | 3.7 | 32.8 | 65.6 |
| R5-3.5:1 | 6-65° C. (mostly 65°) | 22 h | 63.2 | 15.9 | 1.9 | 19.1 | 78.0 |
| 2.3:1 | 62-64° C. | 22 h | 53.6 | 34.6 | 10.4 | 1.3 | 54.4 |
| 2.8:1 | 60-65° C. | 22 h | 70.3 | 20.5 | 3.8 | 5.4 | 74.3 |
| 2.8:1 | 70° C. | 22 h | 78.6 | 12.2 | 2.8 | 6.3 | 84.0 |
| 2.8:1 | 58-60° C. | 22 h | 37.2 | 23.3 | 5.2 | 34.3 | 56.1 |
| 3.2:1 | 52-62° C. (~8-10 h at 52° C.) | 22 h | 51.0 | 20.6 | 2.0 | 26.4 | 69.3 |
| 3.3:1 | 60° C. | 22 h | 35.6 | 1.3 | 0 | 63.2 | 96.4 |
| 3.3:1 | 60-65° C. | 7 h | 22.7 | 9.2 | 1.0 | 67.1 | 69.0 |
| 3.5:1 | ~65-70° C. | 22 h | 70.6 | 7.1 | 1.9 | 20.4 | 88.6 |
| 3.8:1 | 48-63° C. (mostly 48°) | 22 h | 59.4 | 4.7 | 1.6 | 34.3 | 90.4 |
| 4.5:1 | ~55° C. | 22 h | 43.5 | 14.1 | 2.0 | 39.9 | 72.9 |
| 4.5:1 | 58-60° C. | 22 h | 56.3 | 8.5 | 0.9 | 34.4 | 85.7 |
| 4.5:1 | 60-62° C. | 22 h | 65.9 | 2.5 | 0.5 | 31.1 | 95.6 |
| 4.5:1 | 62-64° C. | 22 h | 67.7 | 2.1 | 0.5 | 29.7 | 96.3 |
| 4.5:1 | 60-63° C. | 22 h | 40.5 | 13.2 | 1.6 | 44.6 | 73.2 |
| 4.5:1 | 58-60° C. | 22 h | 1.2 | 0.6 | 3.1 | 95.1 | 24.5 |
| 4.5:1 | 59-64° C. | 20 h | 51.7 | 8.0 | 0.9 | 39.4 | 85.3 |

TABLE 11-continued (Comparative) Transesterification of ethyl ester concentrates to the corresponding triglycerides with 2% NOVOZYME ™ 435.

| EE/Glycerol molar ratio | Incubation temperature | Time (total) | TG | DG | MG | EE | % TG* |
|---|---|---|---|---|---|---|---|
| 4.5:1 | (mostly 59°) 65° C. | 22 h | 69.2 | 1.5 | 0.3 | 29.1 | 97.5 |
| 4.5:1 | 60-62° C. | 22 h | 58.0 | 27.5 | 5.1 | 9.4 | 64.0 |
| 4.5:1 | 60-65° C. | 8 h | 43.6 | 7.3 | 1.0 | 48.2 | 84.0 |
| 5.5:1 | 52-62° C. (mostly 52°) | 22 h | 46.4 | 5.4 | 0.9 | 47.3 | 88.0 |
| 6.2:1 | 60.5° C. | 22 h | 26.0 | 13.1 | 1.2 | 59.7 | 64.5 |
| 6.7:1 | 60° C. | 5 h | 15.2 | 25.7 | 7.5 | 51.6 | 31.4 |
| 7:1 | 55-60° C. (mostly 55°) | 22 h | 1.3 | 1.1 | 2.8 | 94.9 | 25.0 |
| 9.0:1 | 60-62° C. | 22 h | 45.4 | 12.4 | 2.0 | 40.2 | 75.9 |
| ~2.8:1 | 55-67 | 22 h | 66.3 | 19.6 | 4.1 | 10.1 | |
| ~2.8:1 | 70-75 | 22 h | 69.5 | 21.5 | 4.1 | 4.9 | |
| ~2.8:1 | 70-75 | 7 h | 14.0 | 25.6 | 8.1 | 52.3 | |
| ~2.8:1 | 70-75 | 7 h | 5.9 | 26.5 | 12.8 | 54.8 | |
| ~2.8:1 | 50-62 | 22 h | 53.3 | 22.3 | 5.6 | 18.7 | |
| ~2.8:1 | 55-63 | 22 h | 50.7 | 27.1 | 7.0 | 15.2 | |
| ~2.8:1 | 55-65 | 22 h | 47.3 | 29.8 | 6.9 | 16.0 | |
| ~2.8:1 | 55-67 | 22 h | 53.3 | 27.9 | 6.4 | 12.3 | |
| ~2.8:1 | 50-65 | 22 h | 40.1 | 29.3 | 9.2 | 21.4 | |
| ~2.8:1 | 55-67 | 22 h | 59.6 | 25.8 | 5.9 | 8.7 | |
| ~2.8:1 | 55-65 | 22 h | 45.6 | 29.7 | 7.2 | 17.5 | |
| ~2.8:1 | 55-65 | 22 h | 42.0 | 32.6 | 8.1 | 17.3 | |
| ~2.8:1 | 55-65 | 22 h | 47.6 | 29.7 | 6.5 | 16.2 | |
| ~2.8:1 | 55-65 | 22 h | 51.8 | 28.4 | 5.2 | 14.6 | |
| ~2.8:1 | 55-65 | 22 h | 54.3 | 29.1 | 6.0 | 10.6 | |
| ~2.8:1 | 55-65 | 22 h | 51.3 | 28.2 | 6.3 | 14.2 | |
| ~2.8:1 | 55-65 | 22 h | 46.1 | 29.2 | 6.2 | 18.5 | |
| ~2.8:1 | 55-65 | 22 h | 46.7 | 27.5 | 6.3 | 19.4 | |
| ~2.8:1 | 70-75 | 3 h | 7.7 | 28.2 | 7.9 | 56.2 | |
| ~2.8:1 | 70-75 | 22 h | 79.2 | 15.8 | 2.2 | 2.8 | |
| ~2.8:1 | 70-75 | 27 h | 76.6 | 18.1 | 2.4 | 2.9 | |
| ~2.8:1 | 70-75 | 44 h | 79.2 | 16.9 | 1.9 | 2.1 | |
| ~2.8:1 | 70-75 | 48 h | 79.2 | 16.7 | 1.8 | 2.3 | |
| ~2.8:1 | 70-75 | 51 h | 79.7 | 16.9 | 1.6 | 1.8 | |
| ~2.8:1 | 70-75 | 3 h | 18.9 | 38.6 | 9.9 | 32.6 | |
| ~2.8:1 | 70-75 | 22 h | 70.1 | 19.4 | 3.4 | 7.1 | |
| ~2.8:1 | 70-75 | 27 h | 70.4 | 19.8 | 3.3 | 6.5 | |
| ~2.8:1 | 70-75 | 44 h | 75.4 | 16.8 | 3.7 | 4.1 | |
| ~2.8:1 | 70-75 | 48 h | 74.6 | 18.8 | 2.6 | 4.0 | |
| ~2.8:1 | 70-75 | 51 h | 74.6 | 19.0 | 2.5 | 3.9 | |
| ~2.8:1 | 75-80 | 22 h | 80.5 | 13.0 | 2.8 | 3.7 | |
| ~2.8:1 | 75-80 | 27 h | 78.8 | 14.2 | 3.9 | 3.1 | |
| ~2.8:1 | 75-80 | 45 h | 80.7 | 13.9 | 3.0 | 2.5 | |
| ~2.8:1 | 75-80 | 48 h | 79.3 | 16.6 | 1.6 | 2.5 | |
| ~3.0:1 | 70-75 | 22 h | 78.8 | 12.5 | 1.0 | 7.6 | |
| ~3.0:1 | 70-80 | 22 h | 84.1 | 11.6 | 0.7 | 3.6 | |
| ~3.0:1 | 70-80 | 22 h | 74.1 | 15.9 | 1.9 | 8.1 | |
| ~3.0:1 | 70-80 | 22 h | 70.3 | 18.6 | 2.4 | 8.6 | |
| ~3.0:1 | 70-80 | 22 h | 72.5 | 19.5 | 2.3 | 5.7 | |
| ~3.0:1 | 70-80 | 22 h | 81.2 | 15.7 | 1.4 | 1.7 | |
| ~3.0:1 | 75 | 3 h | 29.0 | 30.9 | 2.5 | 35.2 | |
| ~3.0:1 | 75 | 22 h | 74.7 | 13.9 | 2.5 | 8.9 | |
| ~3.0:1 | 75 | 27 h | 75.4 | 14.8 | 2.1 | 7.7 | |
| ~3.0:1 | 75 | 44 h | 82.9 | 11.5 | 1.3 | 4.3 | |
| ~3.0:1 | 75 | 48 h | 83.5 | 11.7 | 0.7 | 4.0 | |
| ~3.0:1 | 75 | 3 h | 46.7 | 26.8 | 6.2 | 20.2 | |
| ~3.0:1 | 75 | 22 h | 69.9 | 18.9 | 2.9 | 8.2 | |
| ~3.0:1 | 75 | 27 h | 71.2 | 19.4 | 2.4 | 7.0 | |
| ~3.0:1 | 75-95 | 17 h | 83.5 | 11.6 | 0.9 | 4.1 | |
| ~3.0:1 | 75-80 | 17 h | 64.5 | 17.9 | 2.0 | 15.5 | |
| ~3.0:1 | 75-80 | 17 h | 60.4 | 25.1 | 3.0 | 11.5 | |
| ~3.0:1 | 75-80 | 17 h | 42.6 | 30.8 | 4.3 | 22.3 | |
| ~3.0:1 | 75-80 | 17 h | 58.4 | 25.3 | 3.1 | 13.3 | |
| ~3.0:1 | 80-95 | 17 h | 80.9 | 12.9 | 2.1 | 4.1 | |
| ~3.0:1 | 80-95 | 22 h | 81.8 | 13.8 | 0.8 | 3.6 | |
| ~3.0:1 | 80-85 | 17 h | 75.2 | 15.2 | 1.8 | 7.8 | |
| ~3.0:1 | 80-85 | 17 h | 71.4 | 20.1 | 1.9 | 6.5 | |
| ~3.0:1 | 80-85 | 17 h | 71.3 | 20.9 | 1.8 | 6.0 | |
| ~3.0:1 | 80-85 | 17 h | 62.9 | 23.2 | 2.3 | 11.7 | |
| ~3.0:1 | 80-85 | 17 h | 11.1 | 0.0 | 0.0 | 88.9 | |
| ~3.0:1 | 80-85 | 17 h | 47.3 | 30.9 | 3.6 | 18.1 | |
| ~3.0:1 | 80-85 | 22 h | 74.5 | 17.7 | 1.3 | 6.6 | |
| ~3.0:1 | 90-95 | 20 h | 52.3 | 28.6 | 3.8 | 15.3 | |
| ~3.0:1 | 80-95 | 17 h | 73.1 | 17.1 | 1.1 | 8.7 | |
| ~3.0:1 | 80-95 | 17 h | 75.2 | 21.9 | 1.7 | 1.3 | |
| ~3.0:1 | 80-95 | 17 h | 78.4 | 18.6 | 1.1 | 1.9 | |
| ~3.0:1 | 80-90 | 17 h | 65.3 | 22.1 | 1.6 | 11.0 | |
| ~3.0:1 | 80-95 | 17 h | 72.4 | 28.6 | 3.8 | 3.2 | |
| ~3.0:1 | 80-95 | 17 h | 73.9 | 22.2 | 1.3 | 2.6 | |
| ~3.0:1 | 80-112 | 17 h | 73.3 | 23.2 | 1.5 | 2.0 | |
| ~3.0:1 | 75-90 | 17 h | 58.8 | 27.9 | 3.0 | 10.3 | |
| ~3.0:1 | 80-95 | 17 h | 73.5 | 18.4 | 0.8 | 7.3 | |
| ~3.0:1 | 80-104 | 17 h | 49.6 | 31.5 | 2.5 | 16.4 | |
| ~3.0:1 | 80-90 | 17 h | 32.1 | 40.0 | 3.1 | 24.8 | |
| ~3.0:1 | 78-90 | 17 h | 12.4 | 49.9 | 3.7 | 34.0 | |
| ~3.0:1 (EE40/20) | 80-90 | 17 h | 4.9 | 56.9 | 1.8 | 36.5 | |
| ~3.0:1 (EE40/20) | 80-90 | 17 h | 1.4 | 32.6 | 17.9 | 48.0 | |
| ~3.0:1 (EE40/20) | 80-92 | 17 h | 1.3 | 19.5 | 21.9 | 57.3 | |
| ~3.0:1 (EE40/20) | 80-90 | 17 h | 1.4 | 5.9 | 10.3 | 82.4 | |

Summary of Results

The recommended reaction temperature is 85° C. The amount of 2% of the enzyme of the reaction mixture mass provided good results and is recommended. However, several experiments indicated that even 1% could be used successfully. Previous experiments indicated that long reaction times (approximately 22 h) provided better results, while shorter periods (e.g., 7 h) seemed to lead to poorer conversions. Conversions at the higher temperatures may require less time. It was observed that lower temperatures produced lower degrees of conversion, e.g., when the temperature dropped during the night to 50° C. (probably due to the fluctuations in the power grid and overnight lowering room temperature). Initially, temperatures around 60° C. were employed. There were temperature fluctuations overnight, and in many cases the temperature was reduced at least to 55° C. The conversions were clearly better at temperatures between 70-75° C. It should be born in mind, that relative initial activity of the enzyme reaches peak around 75° C.

The immobilized enzyme was reused 5 times when 3.5:1 EE/glycerol ratio was used in the presence of 2% of the enzyme. No solvent (e.g., hexane) was used to wash the enzyme for each reaction. Since the enzyme was not washed, there may be a case when the enzyme gets blocked by a component of the reaction mixture.

Throughout this application, various publications are referenced. The disclosures of these publications in their entireties are hereby incorporated by reference into this application.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

SEQUENCE LISTING

```
SEQ ID NO: 1
   1 LPSGSDPAFS QPKSVLDAGL TCQGASPSSV SKPILLVPGT GTTGPQSFDS
           SS       S  S HHHHHHTE EETTBTGGG  SSEEEEE  T T  HHHHHTT

51 NWIPLSTQLG YTPCWISPPP FMLNDTQVNT EYMVNAITAL YAGSGNNKLP
     THHHHHHHTT   EEEEE  TT TT S HHHHH HHHHHHHHHH HHHTTS   EE

101 VLTWSQGGLV AQWGLTFFPS IRSKVDRLMA FAPDYKGTVL AGPLDALAVS
     EEEETHHHHH HHHHHHHTGG GTTTB EEEE ES   TT BST THHHHHTT B

151 APSVWQQTTG SALTTALRNA GGLTQIVPTT NLYSATDEIV QPQVSNSPLD
     HHHHHTBTT  HHHHHHHHH  TTTB SS EE EEE TT SSS      SSSTTT

201 SSYLFNGKNV QAQAVCGPLF VIDHAGSLTS QFSYVVGRSA LRSTTGQARS
     TTTTBTSEEE EHHHHH TT     TTHHHHB HHHHHHHHHH HH SSSS  G

251 ADYGITDCNP LPANDLTPEQ KVAAAALLAP AAAAIVAGPK QNCEPDLMPY
     GGTTGGG    SB TTS HHH HHHHHTHHHH HHHHHHHS   BSS     HH

301 ARPFAVGKRT CSGIVTP
     HHTTTTT EE TTEE
```

What is claimed is:

1. Immobilized enzyme comprising *Candida antartica* lipase B immobilized in a matrix, wherein the matrix comprises a copolymer of divinylbenzene and ethylvinylbenzene or styrene, wherein the matrix has at least 79 weight % divinylbenzene and 4 weight % or less non-polymerizable impurities, wherein the amount of lipase immobilized in the matrix is from 7.5 to 35 KLU/g matrix based on the difference in the enzyme concentration in the solution used to interact with the matrix as measured at 280 nm, and wherein a surfactant is not used in the preparation of the immobilized enzyme.

2. The immobilized enzyme of claim 1, wherein the matrix comprises less than 2% by weight non-polymerizable impurities.

3. The immobilized enzyme of claim 1, wherein enzyme is derived the matrix comprises a copolymer of divinylbenzene and styrene.

4. A method for transesterifying an ester, comprising reacting the ester with an alcohol in the presence of the immobilized enzyme of claim 1, wherein the ester comprises an ester of an unsaturated fatty acid.

5. The method of claim 4, wherein the unsaturated fatty acid is derived from fish oil.

6. The method of claim 4, wherein the unsaturated fatty acid is an omega-3 fatty acid.

7. The method of claim 4, wherein the unsaturated fatty acid is linoleic acid, linolenic acid, gamma-linolenic acid, arachidonic acid, mead acid, stearidonic acid, alpha-eleostearic acid, eleostearic acid, pinolenic acid, docosadienic acid, docosatetraenoic acid, octadecadienoic acid, octadecatrienoic acid, eicosatetraenoic acid, or any combination thereof.

8. The method of claim 4, wherein the unsaturated fatty acid comprises eicosapentaenoic acid 20:5ω3 (EPA), docosahexaenoic acid 22:6ω3 (DHA), docosapentaenoic acid 22:5ω3 (DPA), or any mixture thereof.

9. The method of claim 4, wherein the alcohol is glycerol.

10. The method of claim 4, wherein the enzyme is from 0.1% to 20% by weight of the reaction.

11. The method of claim 4, wherein after the reaction between the ester and the alcohol, the amount of ester that is transesterified is from 70 to 100%.

12. The method of claim 4, wherein the ester comprises an ethyl ester of eicosapentaenoic acid 20:5ω3 (EPA), docosahexaenoic acid 22:6ω3 (DHA), docosapentaenoic acid 22:5ω3 (DPA), or any mixture thereof, and the alcohol comprises glycerol, wherein the ester and the alcohol are present in a molar ratio of from 2:1 to 5:1, wherein the reaction is stirred in the presence of the immobilized enzyme at a temperature of from 70° C. to 90° C. for 20 hours to 24 hours, wherein the matrix comprises a copolymer of divinylbenzene and styrene.

13. A method for esterifying a carboxylic acid, comprising reacting the acid with an alcohol in the presence of the immobilized enzyme of claim 1, wherein the carboxylic acid comprises an unsaturated fatty acid.

14. The method of claim 13, wherein the unsaturated fatty acid is derived from fish oil.

15. The method of claim 13, wherein the unsaturated fatty acid is an omega-3 fatty acid.

16. The method of claim 13, wherein the unsaturated fatty acid is linoleic acid, linolenic acid, gamma-linolenic acid, arachidonic acid, mead acid, stearidonic acid, alpha-eleostearic acid, eleostearic acid, pinolenic acid, docosadienic acid, docosatetraenoic acid, octadecadienoic acid, octadecatrienoic acid, eicosatetraenoic acid, or any combination thereof.

17. The method of claim 13, wherein the unsaturated fatty acid comprises eicosapentaenoic acid 20:5ω3 (EPA), docosahexaenoic acid 22:6ω3 (DHA), docosapentaenoic acid 22:5ω3 (DPA), or any mixture thereof.

18. The method of claim 13, wherein the alcohol is glycerol.

19. The method of claim 13, wherein the enzyme is from 0.1% to 20% by weight of the reaction.

20. The method of claim 13, wherein after the reaction between the carboxylic acid and the alcohol, the amount of carboxylic acid that is esterified is from 70 to 100%.

21. The method of claim 13, wherein the carboxylic acid comprises eicosapentaenoic acid 20:5ω3 (EPA), docosahexaenoic acid 22:6ω3 (DHA), docosapentaenoic acid 22:5ω3 (DPA), or any mixture thereof, and the alcohol comprises glycerol, wherein the ester and the alcohol are present in a molar ratio of from 2:1 to 5:1, wherein the reaction is stirred in the presence of the immobilized enzyme at a temperature of from 60° C. to 90° C. for 2 hours to 24 hours, wherein the matrix comprises a copolymer of divinylbenzene and styrene.

* * * * *